United States Patent
Christensen

(10) Patent No.: US 7,740,602 B2
(45) Date of Patent: Jun. 22, 2010

(54) ANKLE FOOT ORTHOTIC BRACE

(75) Inventor: Roland J. Christensen, Fayette, UT (US)

(73) Assignee: Freedom Innovations, LLC, Irvine, CA (US)

( * ) Notice: Subject to any disclaimer, the term of this patent is extended or adjusted under 35 U.S.C. 154(b) by 424 days.

(21) Appl. No.: 11/270,212

(22) Filed: Nov. 8, 2005

(65) Prior Publication Data

US 2006/0264795 A1 Nov. 23, 2006

Related U.S. Application Data

(60) Provisional application No. 60/626,565, filed on Nov. 9, 2004.

(51) Int. Cl.
*A61F 5/00* (2006.01)
(52) U.S. Cl. .......................... 602/23; 602/27
(58) Field of Classification Search .............. 36/44, 36/178, 181; 602/23, 27–28; 128/882
See application file for complete search history.

(56) References Cited

U.S. PATENT DOCUMENTS

| | | | | |
|---|---|---|---|---|
| 1,354,427 | A | * | 9/1920 | Welter ................... 602/27 |
| 4,517,968 | A | | 5/1985 | Greene et al. |
| 4,688,559 | A | | 8/1987 | Vito et al. |
| 4,938,777 | A | | 7/1990 | Mason et al. |
| 5,088,479 | A | | 2/1992 | DeToro |
| 5,219,324 | A | * | 6/1993 | Hall ..................... 602/28 |
| 5,226,875 | A | * | 7/1993 | Johnson ................. 602/27 |
| 5,429,588 | A | | 7/1995 | Young et al. |
| 5,486,157 | A | | 1/1996 | DiBenedetto |
| 5,509,936 | A | * | 4/1996 | Rappoport et al. ......... 623/27 |
| 5,545,127 | A | | 8/1996 | DeToro |
| 5,609,568 | A | | 3/1997 | Andrews |
| 5,897,515 | A | | 4/1999 | Willner et al. |
| 5,944,679 | A | | 8/1999 | DeToro |
| 6,019,741 | A | | 2/2000 | Prieskorn |
| 6,019,795 | A | | 2/2000 | Phillips |
| 6,083,184 | A | | 7/2000 | Kenosh |
| 6,146,344 | A | | 11/2000 | Bader |
| 6,245,035 | B1 | | 6/2001 | Schrijver |
| 6,267,742 | B1 | | 7/2001 | Krivosha et al. |
| 6,302,858 | B1 | | 10/2001 | DeToro et al. |
| D457,639 | S | | 5/2002 | McCoy |
| 6,676,618 | B2 | | 1/2004 | Andersen |
| 7,266,910 | B2 | * | 9/2007 | Ingimundarson ............ 36/44 |
| 2004/0102727 | A1 | | 5/2004 | Smits |
| 2004/0134500 | A1 | * | 7/2004 | Ingimundarson et al. .... 128/882 |
| 2005/0034327 | A1 | * | 2/2005 | Wolter .................... 36/27 |
| 2005/0234378 | A1 | * | 10/2005 | Ingimundarson et al. .... 602/23 |

\* cited by examiner

*Primary Examiner*—Michael A. Brown
(74) *Attorney, Agent, or Firm*—Thorpe North & Western, LLP

(57) ABSTRACT

An ankle foot orthotic foot brace device includes a primary elongated resistance member attached to and extending from a base disposable under a user's foot. The primary resistance member includes means for attachment to the user's leg, and is deflectable through a deflection range and resilient or elastic to provide an initial resistant force to pivoting of the user's foot with respect to user's leg. A secondary elongated resistance member is engagable by the primary resistance member within a subsequent or distal portion of the deflection range of the primary resistance member. Also included is means for intercoupling the secondary resistance member to the primary resistance member during the subsequent portion of the deflection range of the primary resistance member.

22 Claims, 12 Drawing Sheets

ANKLE FOOT ORTHOTIC BRACE

PRIORITY CLAIM

Benefit is claimed of U.S. Provisional Patent Application No. 60/626,565, filed Nov. 9, 2004, which is herein incorporated by reference.

BACKGROUND OF THE INVENTION

1. Field of the Invention

The present invention relates generally to ankle foot orthotic foot braces, or AFO braces.

2. Related Art

Ankle foot orthotic braces, or AFO braces, have been developed to deal with plantar flexion and dorsiflexion problems, such as from ankle injuries. AFO's are used to improve gait and stability. Some AFO's are plastic and can fit inside a shoe. Other AFO's have double upright metal braces that are built into the shoe itself, or attached to a sole.

Typically, AFOs are either rigid and unbending, or have a hinge at the ankle. Rigid AFO's are designed to keep the foot in the proper position and are often used while the individual is asleep. Hinged AFO's, on the other hand, allow for both free plantar flexion (downward motion) and free dorsiflexion motion (upward motion). Hinged AFO's can also allow free dorsiflexion motion but prevent plantar flexion motion by incorporating a stop in the brace. Some hinged AFO's have a spring to assist in dorsiflexion motion to help lift a dropped foot when a person walks.

While such springs assist in lifting a dropped foot when after a step is completed and the foot is being moved to the next step, such springs can also interfere with finishing a step because the spring tends to pull the toe upward when the user is naturally pushing downward with the toe. Furthermore, such spring assist AFO's create a very unnatural heel strike or downward movement of the foot because the toe is biased into an upward position, resulting in a very hard heel strike.

SUMMARY OF THE INVENTION

It has been recognized that it would be advantageous to develop an ankle foot orthotic foot brace or AFO brace capable for providing softer heel strike and stiffer toe off.

The invention provides an ankle foot orthotic foot brace device. The device includes a primary elongated resistance member attached to and extending from a base disposable under a user's foot. The primary resistance member includes means for attachment to the user's leg, and is deflectable through a deflection range and resilient or elastic to provide an initial resistant force to pivoting of the user's foot with respect to user's leg. A secondary elongated resistance member is engagable by the primary resistance member within a subsequent or distal portion of the deflection range of the primary resistance member. Also included is means for intercoupling the secondary resistance member to the primary resistance member during the subsequent portion of the deflection range of the primary resistance member.

Additional features and advantages of the invention will be apparent from the detailed description which follows, taken in conjunction with the accompanying drawings, which together illustrate, by way of example, features of the invention.

DETAILED DESCRIPTION

Figure 1:
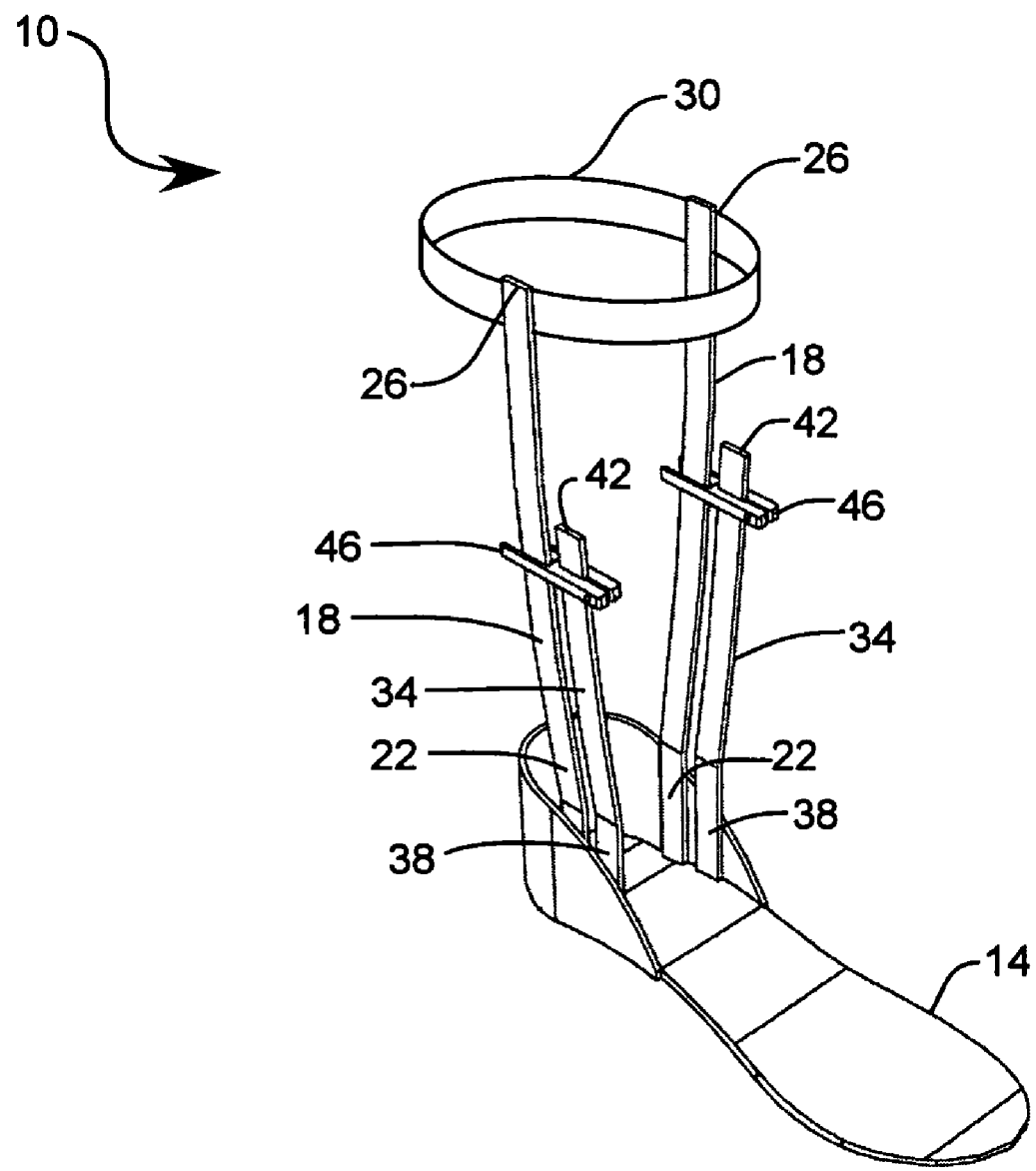
FIG. 1 is a perspective view of an ankle foot orthotic in accordance with an embodiment of the present invention.
Figure 2:
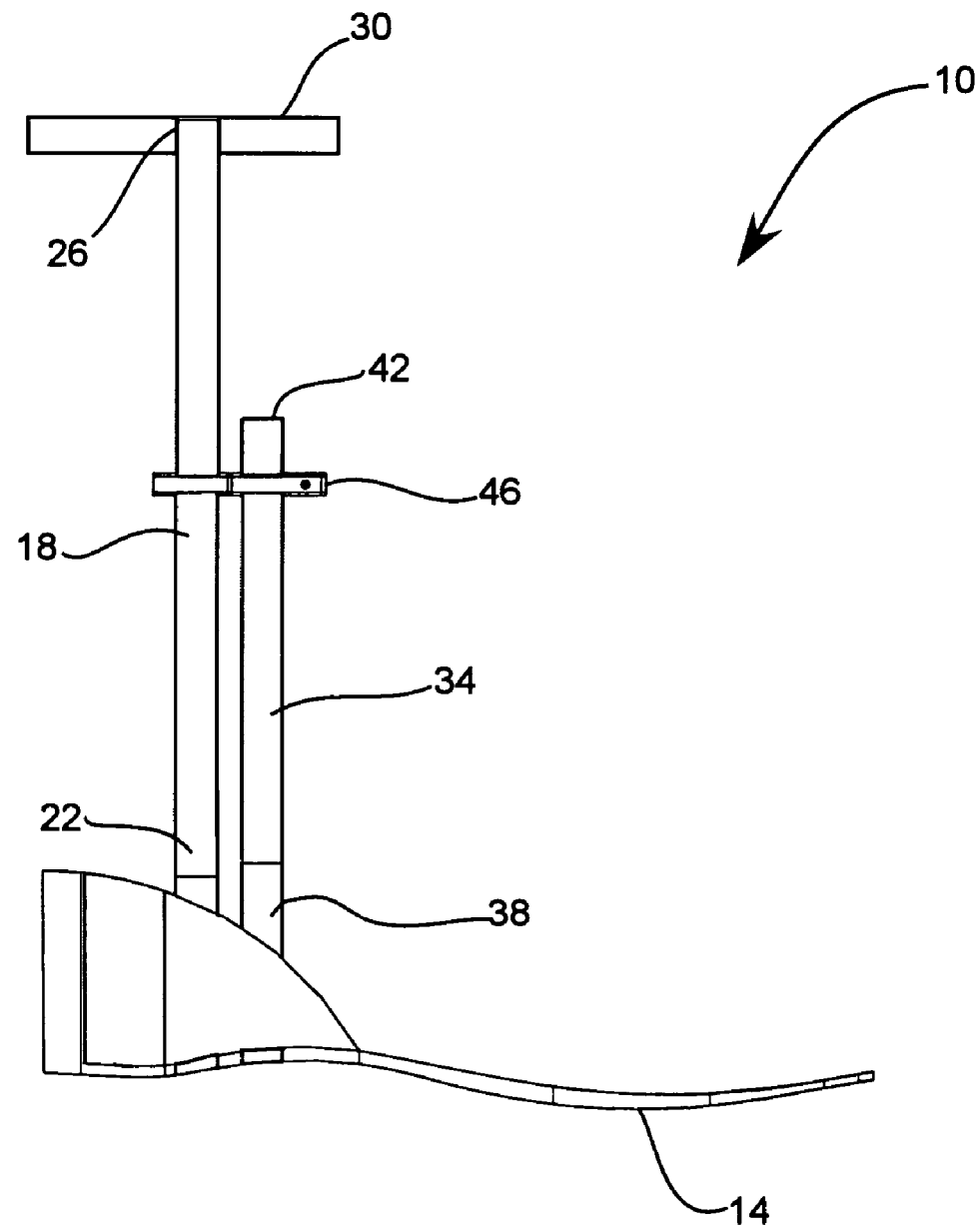
FIG. 2 is a side view of the ankle foot orthotic of FIG. 1.
Figure 3:
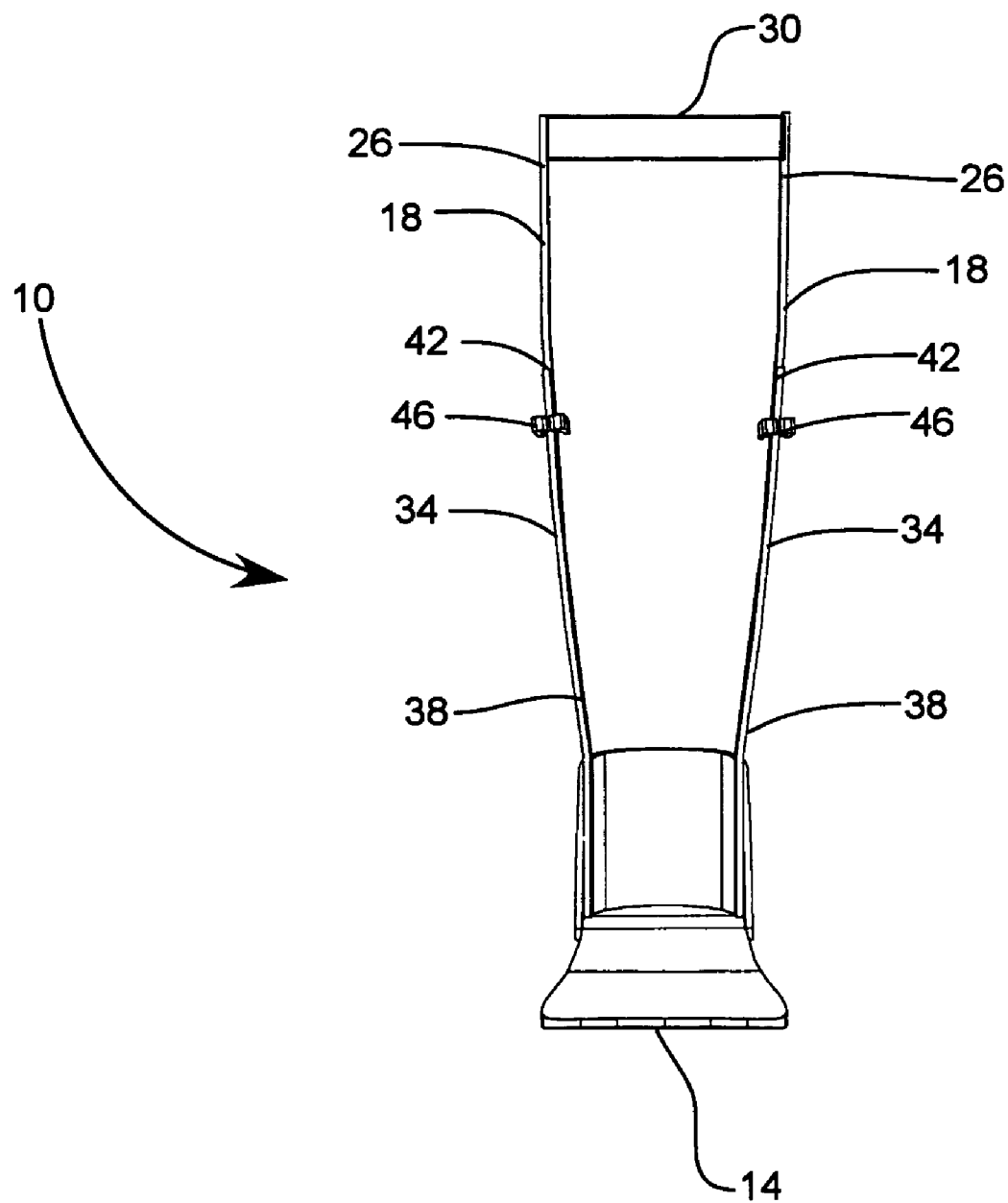
FIG. 3 is a front view of the ankle foot orthotic of FIG. 1.
Figure 4:
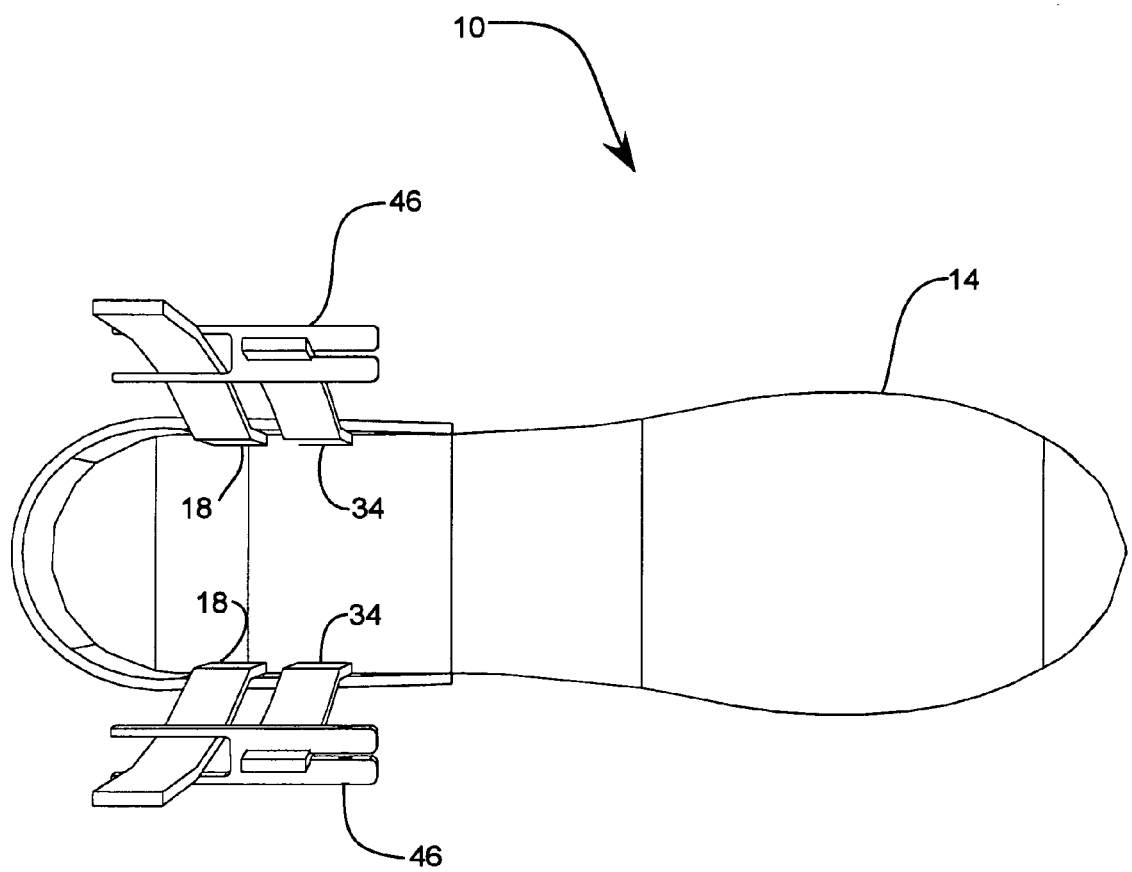
FIG. 4 is a top view of the ankle foot orthotic of FIG. 1.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1-4, an ankle foot orthotic brace, indicated generally at 10, in accordance with the present invention is shown. Ankle rehabilitation is an example of one field that might benefit from the use of such a brace.

The ankle foot orthotic brace device includes a base or foot plate 14 to be disposed under a user's foot, and/or between the user's foot and a shoe worn on the user's foot. The base or foot plate 14 can be generally horizontally disposed and can have a length to extend substantially the length of the user's foot. Alternatively, the foot plate 14 can be shorter and can extend only across a portion of the user's foot. In addition, the foot plate 14 can be configured or shaped with an arcuate profile to match the user's foot, and to provide a comfortable feel. Furthermore, the foot plate 14 can include a cup portion to receive the user's heel.

A primary elongated spring, strut, or rib 18 can have a proximal end 22 attached to the foot plate 14, and a distal end 26 extending substantially vertically therefrom and configured to be coupled to the user's leg. A strap 30 can be coupled to the distal end 26 of the primary spring member 18 and can extend around the user's leg, and fasten upon itself, such as with hook-and-loop type fastener, snaps, buckle, or the like. The strap 30 is an example of means for attachment to the user's leg. Another means for attachment can include an integral sock, or expandable elastic loop.

The primary spring member 18 is flexible to deflect or bend as the user's ankle pivots, and resilient or elastic to provide a resistance force to deflection and movement between the user's foot and leg. The spring member 18 can deflect through a deflection range. For example, the spring member 18 can deflect rearwardly during heel strike, and forwardly during toe off. The primary spring member 18 can be or can include a composite material with a fiber in a resin matrix, such as graphite.

The primary spring member 18 can be disposed on a side of the base or plate 14, and thus on the side of the user's foot. Alternatively, the primary spring member 18 can be disposed at the rear of the plate 14, and behind the user's foot. A pair of primary spring members 18 can be provided on each side of the foot, as shown in FIGS. 1-4.

A secondary elongated spring member 34, such as a strut or rib, can have a proximal end 38 attached to the foot plate 14, and can extending substantially vertically therefrom to a distal end 42 configured to be engaged by the primary spring member 18. The secondary spring member 34 is similar in many respects to the primary spring member 18. The secondary spring member 34 is flexible to deflect, and resilient or elastic to provide additional resistance force to deflection and movement when engaged by the primary spring member 18. The distal end 42 of the secondary spring member 34 is not coupled to the user's leg, as with the primary spring member. While the primary spring member 18 deflects rearwardly during heel strike, the secondary spring member 34 does not. But while the primary spring member 18 deflects forwardly during toe off, it engages the secondary spring member 34 and the secondary spring member 34 deflects, providing additional resistance force, and a stiffer response. Thus, the secondary spring member 34 can be disposed in a distal or subsequent portion of the deflection range of the primary spring member 18. The secondary spring member 34 can also be or can include a composite material.

The secondary spring member 34 can be spaced-apart from the primary spring member 18, and positioned so that the primary spring 18 engages the secondary spring 34 during a distal or subsequent portion of the deflection range. The secondary spring member 34 can be disposed forwardly of the primary spring member 18, as shown. The primary spring member 18 can be placed behind the secondary spring member 34 so that the primary spring member 18 can deflect rearwardly without engaging the secondary spring member 34 during heel strike, and can deflect forwardly to engage the secondary spring member 34 during toe off.

In addition, the secondary spring 34 can be disposed on the side of the foot plate 14, and on the side of the user's foot. Alternatively, the secondary spring member 34 can be disposed on the back 50 of the foot plate 14 and behind the user's foot. Alternatively, the primary spring member 18 can be disposed behind the foot, while the secondary spring member 34 is disposed on the side of the foot. In addition, a pair of secondary spring members 34 can be provided.

Thus, it will be appreciated that the primary and secondary spring members 18 and 34 are arranged to provide for a softer heel strike and a stiffer toe off. The primary spring member 18 is one example of primary means for resisting primary movement and displacement between the user's foot and leg through a deflection range in order to provide an initial resistant force to pivoting of the user's foot with respect to user's leg. The secondary spring member 34 is one example of secondary means for increasing resistance to subsequent movement between the user's foot and leg that is engagable by the primary means within a subsequent deflection range of the user's leg, in order to provide a secondary resistant force to pivoting of the user's foot with respect to user's leg.

A yoke 46 can be secured to the secondary spring member 34. Alternatively, the yoke 46 can be secured to the primary spring member 18. The yoke 46 can include a pair of arms defining a slot therebetween to receive the primary spring member (or secondary spring member). Thus, the yoke 46 can provide a guide to coordinate deflection between the primary and secondary spring members 18 and 34.

In addition, the yoke 46 can be slidably or adjustably positioned along the length of the secondary spring member 34 (or primary spring member 18). For example, the secondary spring member 34 can be received in an aperture or slot 54 of the yoke 46. The aperture or slot 54 can be split so that it can be compressed or expanded with a screw. Thus, the yoke 46 can be tightened or loosened on the spring member. The yoke 46 can be selectively adjusted to adjust engagement of the secondary spring member 34, and thus to adjust the stiffness of the toe off. The yoke 46 is one example of means for selectively adjusting the engagement of the secondary spring member 34 by the primary spring member 18. The split aperture 54 with screw is an example of one means for selectively adjusting the means for intercoupling.

Figure 5:
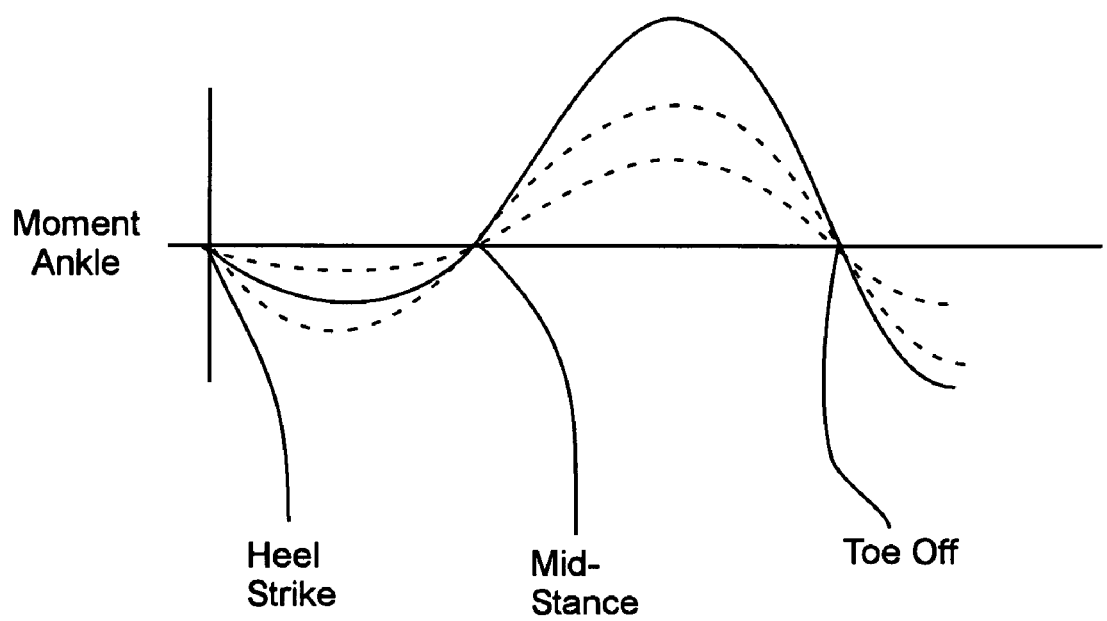
FIG. 5 is a graph of the moment of the ankle versus position of the foot from heel strike to toe off.

Referring to FIG. 5, a moment curve of the brace 10 is shown with respect to other braces. It can be seen that the secondary spring member 34 provides a reinforcing stiffening member to increase toe stiffness with respect to heel stiffness, and to adjust heel moment with respect to toe moment. Furthermore, the AFO braces 10 provide lesser resistance or energy storage and release to ankle pivoting at heel strike, and greater resistance or energy storage and release at toe off. Prior braces have been found to provide substantially the same response or opposite response to heel strike and toe off. It has also been found that the brace 10 of the present invention helps with proper rotation of the foot during walking.

Figure 6:
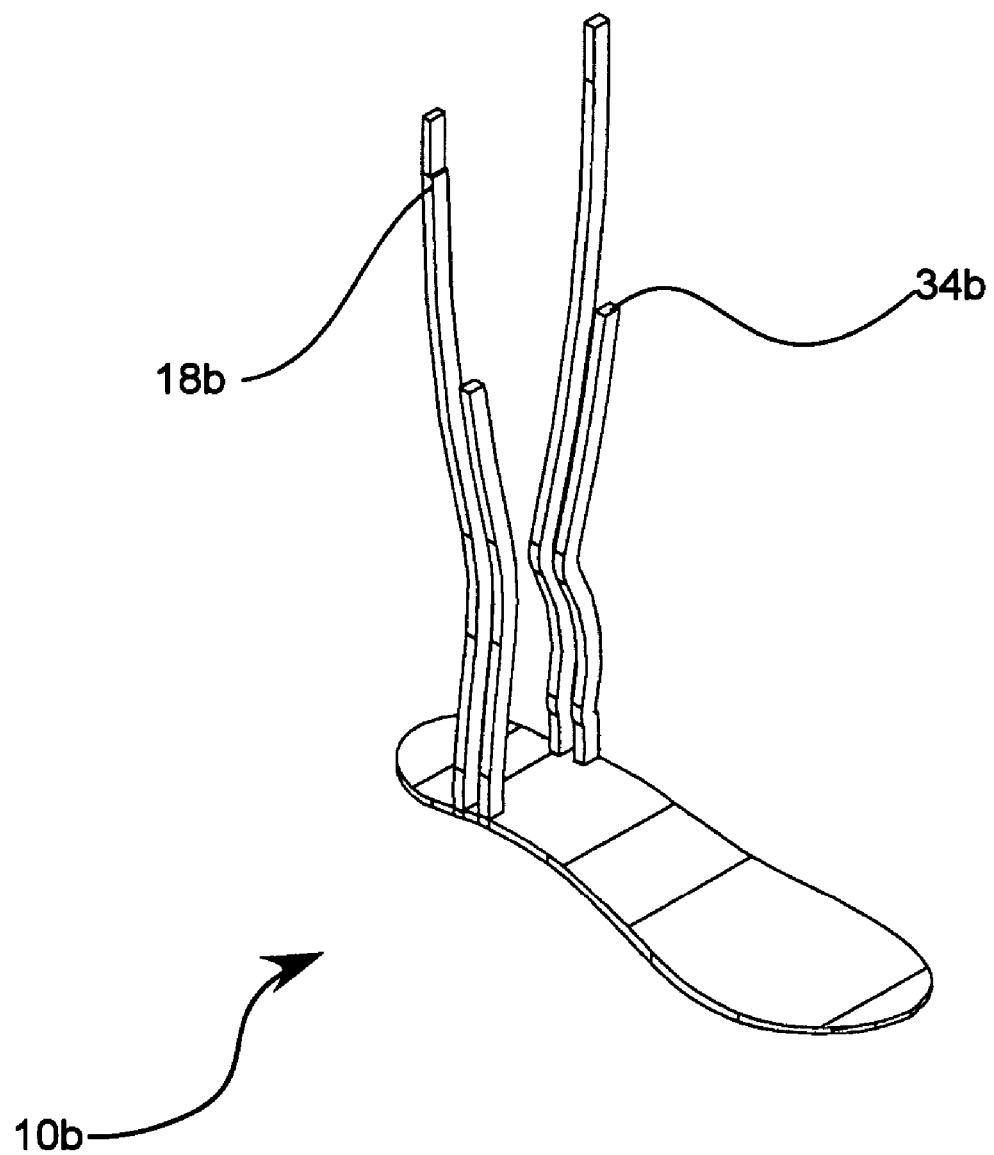
FIG. 6 is a perspective view of another ankle foot orthotic in accordance with an embodiment of the present invention.

Referring to FIG. 6, another ankle foot orthotic brace 10*b* is shown that is similar to that described above, but has primary and secondary spring members 18*b* and 34*b* that are shaped or configured to match the shape of the user's leg.

Figure 7:
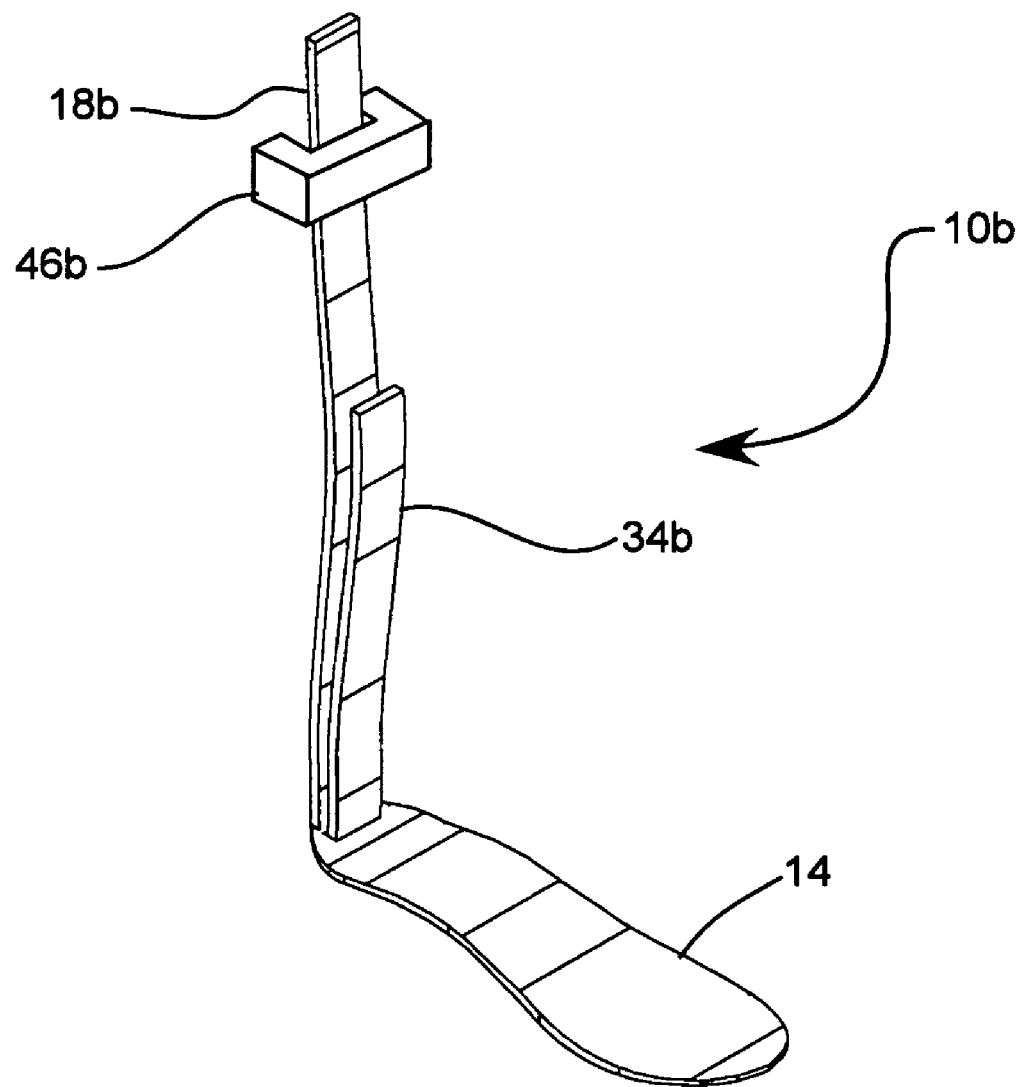
FIG. 7 is a perspective view of another ankle foot orthotic in accordance with an embodiment of the present invention.
Figure 8:
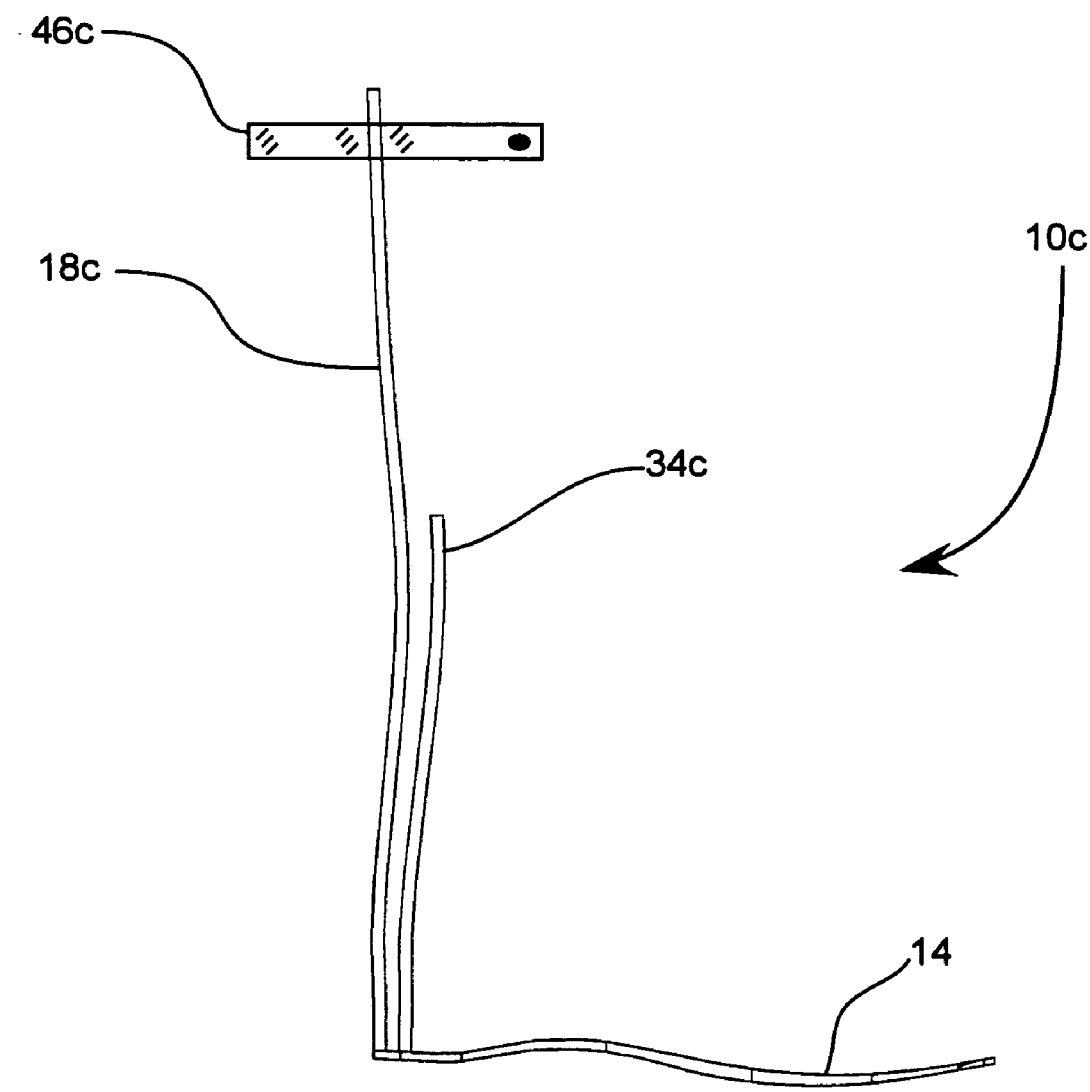
FIG. 8 is a side view of the ankle foot orthotic of FIG. 7.

Referring to FIGS. 7 and 8, another ankle foot orthotic brace 10*c* is shown that is similar to those described above, but has the primary and secondary spring members 18*c* and 34*c* disposed at the rear of the user's foot, as indicated above. A similar slide or yoke 46*c* can be used to selectively adjust the engagement of the secondary spring member 34*c* by the primary spring member 18*c*.

Figure 9:
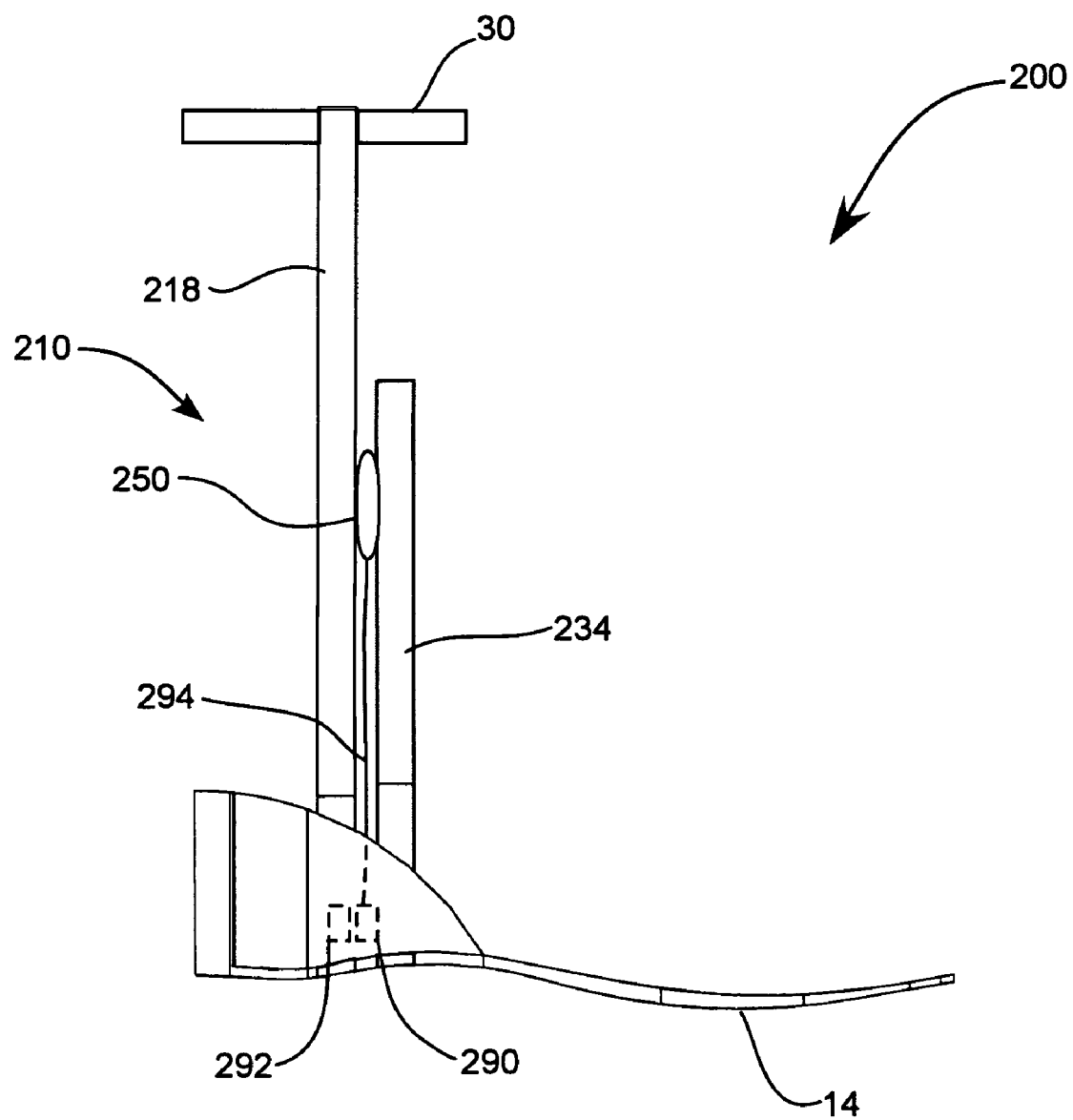
FIG. 9 is a side view of another ankle foot orthotic in accordance with another embodiment of the present invention.

Referring to FIG. 9, another ankle foot orthotic brace 200 is shown that is similar to those described above, but has a variable energy transfer medium, shown generally at 210, disposed between the primary resistance member 218 and secondary resistance member 234. An example of such a variable energy transfer medium is described in U.S. Pat. No. 6,663,673, which is herein incorporated by reference. The variable energy transfer medium 210 can transfer at least some energy from the primary resistance member 218 to the secondary resistance member 234 during use.

As shown in FIG. 9, the variable energy transfer medium 210 can include a flexible bladder 250 disposed between the primary resistance member 218 and secondary resistance member 234. A variable viscosity fluid can be disposed in the flexible bladder 250 to variably transfer energy between the primary resistance member 218 and secondary resistance member 234 during use. The variable viscosity fluid can increase viscosity with an increase in a load factor applied to the primary resistance member 218 or secondary resistance member 234 to transfer more energy between the primary and secondary resistance members 218 and 234 during the increase in the load factor. Similarly, the variable viscosity fluid can decrease viscosity during a decrease in the load factor applied to the primary or secondary resistance members 218 and 234 to transfer less load between the primary and secondary resistance members during a decrease in the load factor.

The variable viscosity fluid can be a magneto rheologic fluid responsive to a magnetic field, or an electro rheologic fluid responsive to an electric field. A sensor 290 can be coupled to the ankle foot orthotic to sense a load factor in either the primary or secondary resistance members 218 or 234. Control electronics 292 can be coupled to the sensor 290 and the variable viscosity fluid to apply an electric or magnetic field in response to the load factor sensed by the sensor. The electric or magnetic field can interact with the electro or magneto rhelogic fluid to increase the viscosity of the fluid thereby transferring more energy between the primary and secondary resistance members. A power source 294, such as a battery, can be coupled to the sensor and control electronics.

The energy transfer medium, or variable viscosity fluid or material, is located between first and second members so that energy is transferred between the first and second members, and thus through the energy transfer medium, during use. The variable viscosity of the fluid or material advantageously allows the energy transferred between the members to be varied, thus varying the stiffness or response. The variable viscosity fluid can increase in viscosity with an increase in a load factor applied to the variable viscosity fluid. Such load factors can include a load, a load rate, a strain, a strain rate, a pressure, a deflection, etc. The variable viscosity fluid or material can include a shear stiffening material that increases in viscosity as load or strain, or load rate or strain rate, is applied; an electro rheologic fluid that changes viscosity under an applied electric field; or a magneto rheologic fluid that changes viscosity under an applied magnetic field.

The variable viscosity fluid or material can include a shear stiffening material. Such a shear stiffening material increases in viscosity as a load or strain (or load or strain rate) is applied, or as the load or strain increases. An example of such shear stiffening material is a composition of cornstarch and water. Under little or no load or strain, the shear stiffening material can be less viscous and capable of greater flow, and thus can be displacable while the energy transfer medium can be compressible. Under greater load or strain, the shear stiffening material can be more viscous and less capable of flowing, and thus can be less displacable while the energy transfer medium can be less compressible. It will be appreciated that the less-viscous shear stiffening material dissipates more energy or force so that less energy or force is transferred by the material. Similarly, the more-viscous shear stiffening material transfers more energy or force.

The variable viscosity fluid or material can include an electro rheologic fluid that is responsive to an applied electric field to alter its viscosity. Such an electro rheologic fluid increases in viscosity as an electric field is applied. Under little or no electric field, the electro rheologic fluid can be less viscous and capable of greater flow, and thus can be displacable. Under a greater electric field, the electro rheologic fluid can be more viscous and less capable of flowing, and thus can be less displacable. Again, it will be appreciated that the less-viscous electro rheologic fluid dissipates more energy or force so that less energy or force is transferred by the fluid. Similarly, the more-viscous electro rheologic fluid transfers more energy or force.

A transducer, such as a strain gauge, coupled to the first and/or second member. The transducer senses strain or deformation in the member. The transducer can be operatively coupled to control electronics and a power source. The control electronics and transducer can be operatively coupled to the electro rheologic fluid, such as by electrodes coupled to the bag. The control electronics can include amplifier circuitry, while the power source can be a battery. The transducer senses deflection or strain in the first and/or second members and produces a signal that can be sent to the control electronics. The control electronics can include amplifier circuitry to amplify the signal to create a control signal. In addition, the control electronics can include circuitry to accept only signals that correspond to a predetermined minimum strain or deflection. The control signal can be applied to the electro rheologic fluid by the electrodes. It will be appreciated that the control electronics can include inputs to vary the amplification, minimums, etc., to control or customize the energy transfer of the fluid, and the stiffness of the device.

Alternatively, the transducer can be coupled to the energy transfer medium or the bag or bladder containing the variable viscosity fluid. Thus, the transducer can be configured to sense pressure of the variable viscosity fluid in the bladder. Similarly, the transducer can be configured to sense deflection of the energy transfer medium.

Such an electro rheologic fluid can include particles or filings in an oil. As the electric field is applied, the particles or filings align, increasing the viscosity of the fluid, or the oil with particles or filings. With no or little electrical field, the particles or filings are random, decreasing the viscosity of the fluid, or the oil with particles or filings.

The variable viscosity fluid or material can include a magneto rheologic fluid that is responsive to an applied magnetic field to alter its viscosity. Such a magneto rheologic fluid increases in viscosity as a magnetic field is applied. Under little or no magnetic field, the magneto rheologic fluid can be less viscous and capable of greater flow, and thus can be displacable. Under a greater magnetic field, the magneto rheologic fluid can be more viscous and less capable of flowing, and thus can be less displacable. Again, it will be appreciated that the less-viscous magneto rheologic fluid dissipates more energy or force so that less energy or force is transferred by the fluid. Similarly, the more-viscous magneto rheologic fluid transfers more energy or force.

The magnetic field can be applied by magnets that are operatively coupled to the bag. The magnets can be electromagnets operatively coupled to the control electronics using the control signal to generate the magnetic field. Such a magneto rheologic fluid can include particles or filings in an oil. As the magnetic field is applied, the particles or filings align, increasing the viscosity of the fluid, or the oil with particles or filings. With little or no magnetic field, the particles or filings are random, decreasing the viscosity of the fluid, or the oil with particles or filings.

The electro rheologic fluid can be forced through, or can pass through, an orifice and into a reservoir under the loading of the device. The electrodes can be disposed around the orifice to apply and electric field at or near the orifice. The electro rheologic fluid is responsive to the applied electric field to alter its viscosity. Such an electro rheologic fluid increases in viscosity as the electric field is applied, thus impeding the flow of the fluid through the orifice. Under little or no electric field, the electro rheologic fluid can be less viscous and capable of greater flow, and thus can pass through the orifice. Therefore, under lesser force or load, the fluid flows through the orifice for less energy transfer, and a softer feel. Under a greater electric field, the electro rheologic fluid can be more viscous and less capable of flowing, and thus is impeded from flowing through the orifice. Therefore, under greater force or load, the fluid is impeded from flowing through the orifice for more energy transfer and a stiffer feel.

The magneto rheologic fluid can be forced through, or can pass through, an orifice and into a reservoir under the loading. The magnets can be disposed around the orifice to apply a magnetic field at or near the orifice. The magneto rheologic fluid is responsive to the applied magnetic field to alter its viscosity. Such a magneto rheologic fluid increases in viscosity as the magnetic field is applied, thus impeding the flow of the fluid through the orifice. Under little or no magnetic field, the magneto rheologic fluid can be less viscous and capable of greater flow, and thus can pass through the orifice. Therefore, under lesser force or load, the fluid flows through the orifice for less energy transfer, and a softer feel. Under a greater magnetic field, the magneto rheologic fluid can be more viscous and less capable of flowing, and thus is impeded from flowing through the orifice. Therefore, under greater force or load, the fluid is impeded from flowing through the orifice for more energy transfer and a stiffer feel.

Figure 10:
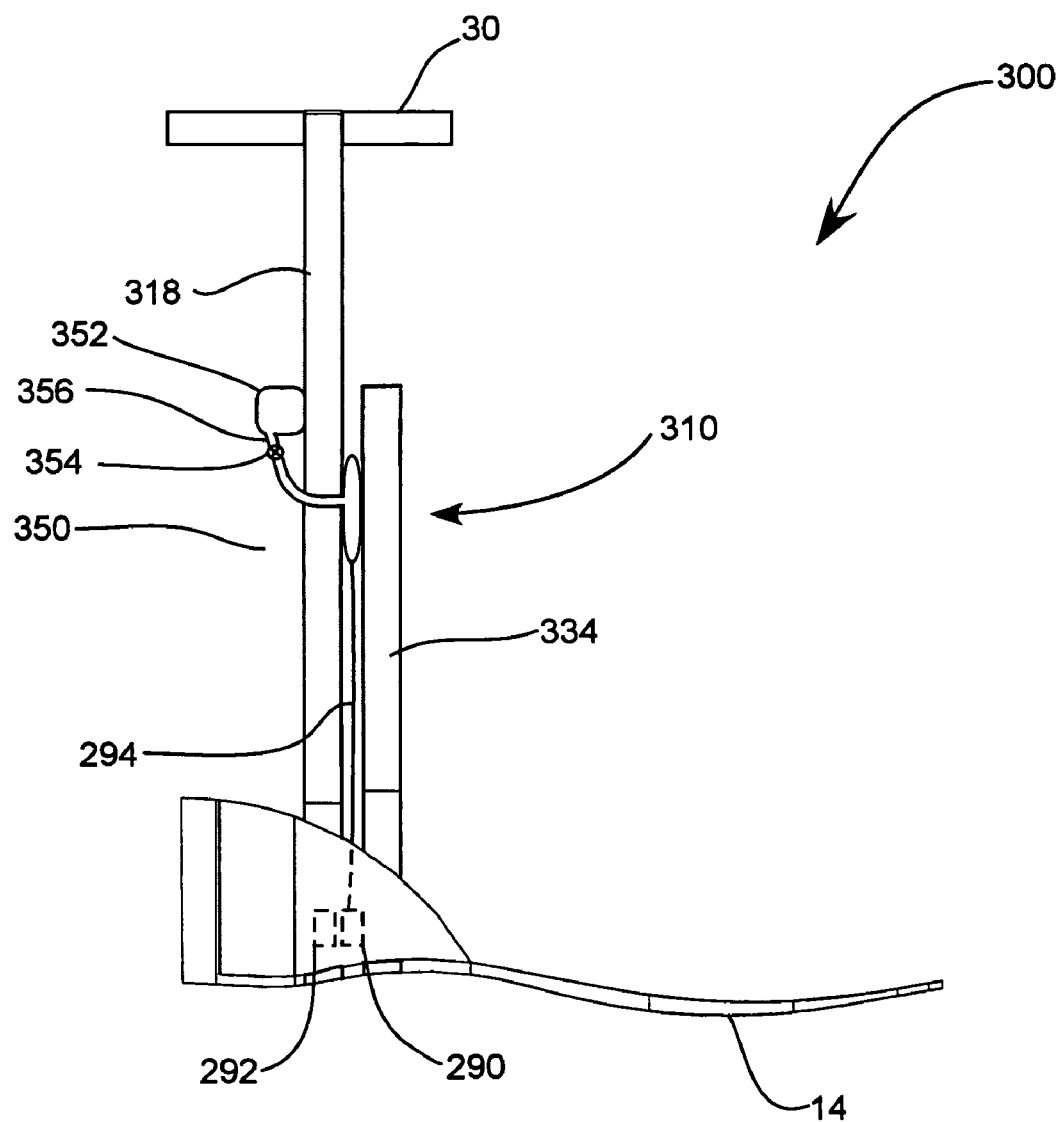
FIG. 10 is a side view of another ankle foot orthotic in accordance with another embodiment of the present invention.
Figure 11:
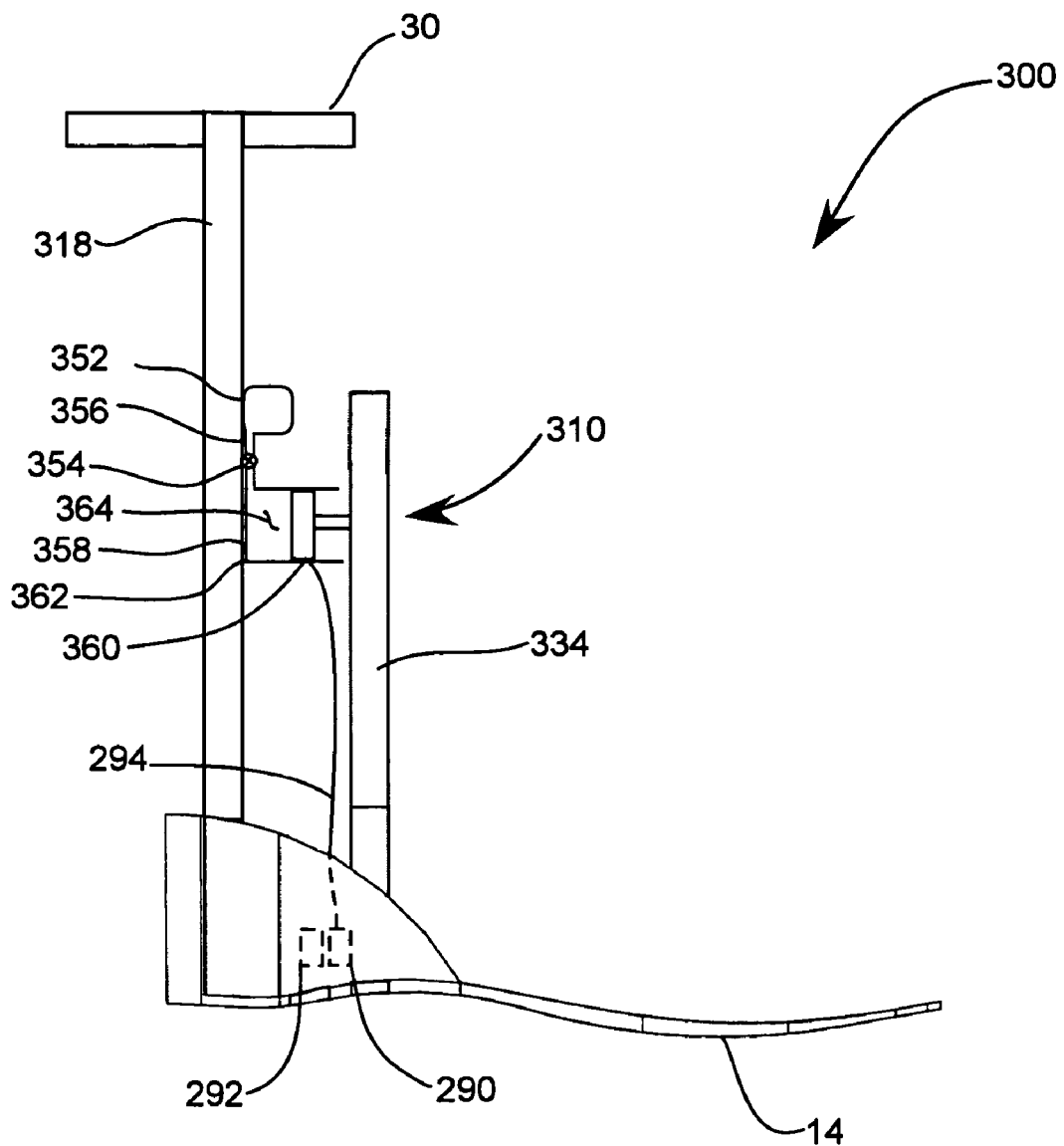
FIG. 11 is a side view of another ankle foot orthotic in accordance with another embodiment of the present invention.

Referring to FIGS. 10-11, another ankle foot orthotic brace 300 is shown that is similar to those described above, but has a variable energy transfer medium, shown generally at 310, disposed between the primary resistance member 318 and secondary resistance member 334, as described in U.S. patent application Ser. No. 11/098,828 filed on Apr. 4, 2005, which is herein incorporated by reference.

The variable energy transfer medium can include an enclosure disposed between the primary and secondary resistance members 318 and 334. In one aspect, as shown in FIG. 10, the enclosure can be a flexible bladder 350 similar to the flexible bladder 250 described above. A fluid path 356 can be in fluid communication with the enclosure 350. A reservoir 352 can be in fluid communication with the fluid path 356. A fluid can be disposed in the enclosure and displaceable to the reservoir through the fluid path in response to an applied force to the primary or secondary resistance member 318 or 334. A variable orifice 354 with a variable size can be disposed in the fluid path to control the displacement of the fluid between the enclosure 350 and the reservoir 352.

Thus, in use, as a force is applied to the primary or secondary resistance member 318 or 334, fluid is displaced between the enclosure 350 and the reservoir 352. The rate of displacement of the fluid between the enclosure 350 and the reservoir 352, as controlled by the variable orifice 354, corresponds to the transfer of energy between the primary and secondary resistance members 318 and 334. For example, a high rate of displacement of fluid, corresponding to a more open orifice size, can transfer less energy between the primary and secondary resistance members and gives the ankle foot orthotic a squishier or softer feel to the step of the user. Similarly, a low rate of displacement of fluid, corresponding to a more closed orifice size, can transfer more energy between the primary and secondary resistance members and gives the ankle foot orthotic a stiffer or harder feel to the step of the user.

The variable orifice 354 is one means for variably resisting fluid flow between the enclosure and the reservoir to variably transfer the applied force from the primary resistance member 318 to the secondary resistance member 334.

In another aspect, as shown in FIG. 11, the enclosure 358 can be a piston 369 in a cylinder 362. The piston can form a chamber 364 with the piston. Fluid can flow between the chamber and the reservoir 352 in response to forces applied primary and secondary resistance members. A variable orifice 354 can control the rate of flow between the enclosure and the reservoir as described above.

Figure 12:
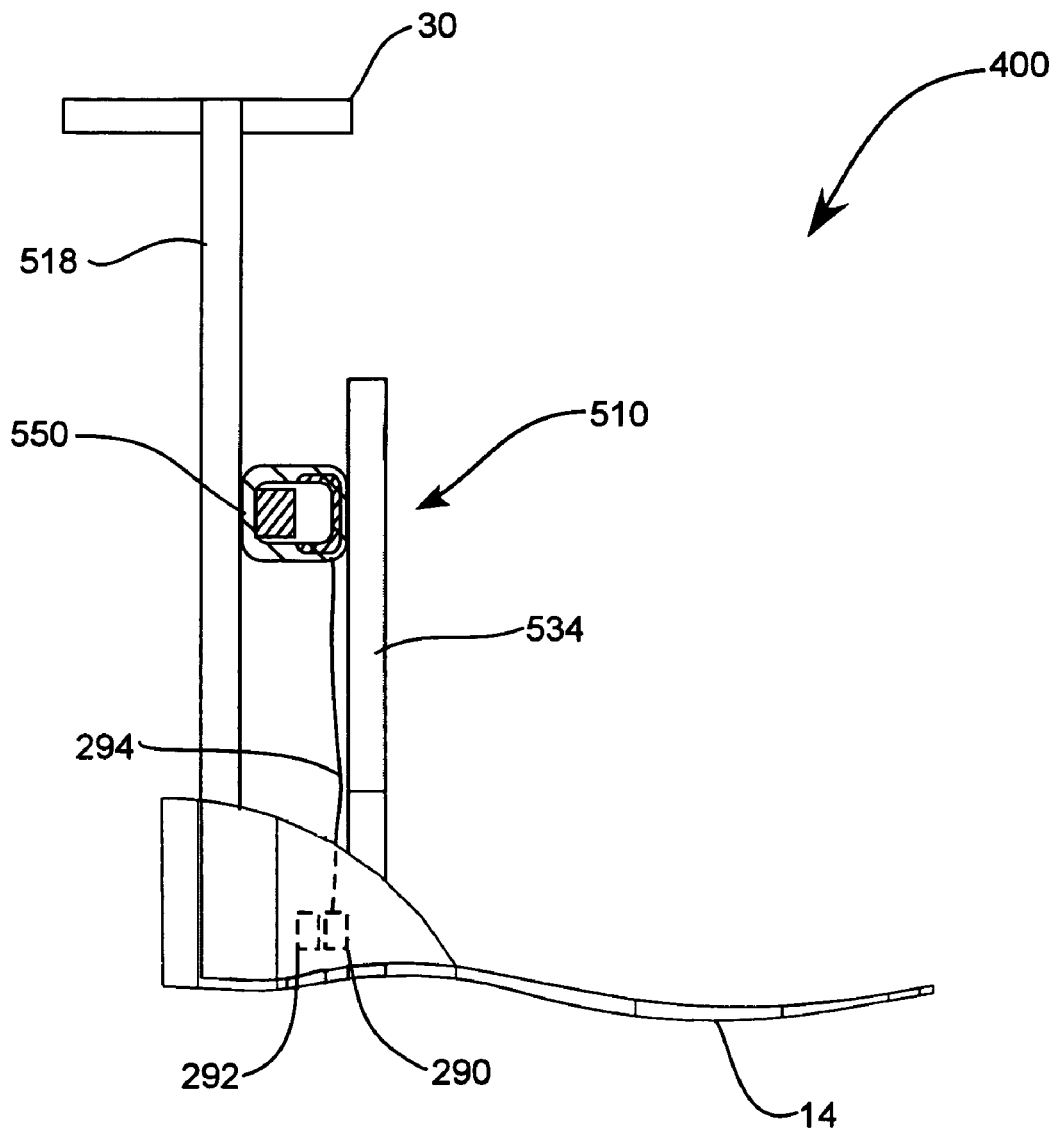
FIG. 12 is a side view of another ankle foot orthotic in accordance with another embodiment of the present invention.

Referring to FIG. 12, another ankle foot orthotic brace 400 is shown that is similar to those described above, but has a variable energy transfer medium, shown generally at 510, disposed between the primary resistance member 518 and secondary resistance member 534, as described in U.S. Pat. No. 6,875,241 which is herein incorporated by reference. As illustrated in FIG. 12, the energy transfer medium 510 can be a variable resistance cell 550 that can provide a variable resistance response to a load factor.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. An ankle foot orthotic brace device, comprising:
    a) a base, engagable by a user's foot;
    b) a rearward elongated resistance member, having one end attached to the base and extending to an opposite end attachable to the user's leg, being deflectable through a deflection range and resilient to provide a primary resistant force to deflection of the rearward member with respect to the base and pivoting of the user's foot with respect to user's leg; and
    c) a forward elongated resistance member disposed forwardly of the rearward member and engagable by the rearward member within a subsequent deflection range of the rearward member in a forward direction, and spaced apart from the rearward resistance member forwardly with respect to the rearward member along an entire length of the forward resistance member; and
    d) the forward and rearward resistance members include a composite material with a fiber in a resin matrix.

2. A device in accordance with claim 1, further comprising:
    means for intercoupling the forward resistance member to the rearward resistance member during the subsequent portion of the deflection range of the rearward resistance member.

3. A device in accordance with claim 2, wherein the means for intercoupling includes a yoke secured to one of the forward or rearward resistance members.

4. A device in accordance with claim 3, wherein the yoke is slidably or adjustably positioned along one of the forward or rearward resistance members.

5. A device in accordance with claim 3, wherein the yoke includes a pair of arms defining a slot therebetween to receive one of the forward or rearward resistance members.

6. A device in accordance with claim 1, wherein the forward and rearward resistance members are spaced apart from one another a predetermined distance so that the rearward resistance member can deflect a predetermined amount before engaging the forward resistance member.

7. A device in accordance with claim 1, wherein the rearward resistance member is placed behind the forward resistance member so that the rearward resistance member can deflect rearwardly without engaging the forward resistance member during heel strike, and can deflect forwardly to engage the forward resistance member during toe off.

8. A device in accordance with claim 1, further comprising:
    means for selectively adjusting the engagement of the forward resistance member by the rearward resistance member.

9. A device in accordance with claim 1, wherein the forward and rearward resistance members are arranged to provide for a softer heel strike and a stiffer toe off.

10. A device in accordance with claim 1, wherein the forward and rearward resistance members are disposed on a common side of the base and extend along a side of the user's foot and leg.

11. A device in accordance with claim 1, wherein the forward and rearward resistance members are disposed on a back of the base and extend along a back of the user's foot and leg.

12. A device in accordance with claim 1, further comprising means for attachment including a strap securable around the user's leg.

13. A device in accordance with claim 1, further comprising:
- a variable energy transfer medium disposed between the forward and rearward resistance members to transfer at least some energy from the forward resistance member to the rearward resistance member during use.

14. A device in accordance with claim 13, wherein the variable energy transfer medium further includes:
- a flexible bladder disposed between the forward and rearward resistance members; and
- a variable viscosity fluid, disposed in the flexible bladder, to variably transfer energy between the forward and rearward resistance members during use, the variable viscosity fluid being capable of increasing viscosity with an increase in a load factor to transfer more energy between the forward and rearward resistance members during the increase in the load factor and being capable of decreasing viscosity during a decrease in the load factor to transfer less load between the forward and rearward resistance members during a decrease in the load factor.

15. A device in accordance with claim 14, wherein the variable viscosity fluid includes at least one fluid selected from the group consisting of: a magneto rheologic fluid responsive to a magnetic field, or an electro rheologic fluid responsive to an electric field.

16. A device in accordance with claim 14, further comprising:
- a sensor to sense a load factor; a power source, coupled to the sensor; and control electronics, coupled to the sensor and the variable viscosity fluid, to apply an electric or magnetic field in response to the load factor sensed by the sensor.

17. A device in accordance with claim 13, wherein the variable energy transfer medium further includes:
- a variable resistance cell configured to provide a variable resistance response to a load factor.

18. A device in accordance with claim 13, wherein the variable energy transfer medium further includes:
- a) an enclosure, disposed between the forward and rearward resistance members;
- d) a fluid path, in fluid communication with the enclosure;
- e) a reservoir, in fluid communication with the fluid path;
- f) a fluid, disposed in the enclosure and displaceable to the reservoir through the fluid path in response to the applied force; and
- g) means for variably resisting fluid flow between the enclosure and the reservoir, to variably transfer the applied force from the rearward resistance member to the forward resistance member.

19. A device in accordance with claim 18, wherein the means for variably resisting fluid flow further comprises a fluid displaceable through a variable orifice with a variable size.

20. A device in accordance with claim 1, wherein the rearward member is deflectable rearwardly without engaging the forward member.

21. A device in accordance with claim 1, wherein the rearward member is couplable to a user's leg, while the forward member is not couplable to the user's leg, so that the rearward member is deflectable rearwardly and forwardly with the user's leg, while the forward member is only deflectable forwardly when engaged by the rearward member.

22. An ankle foot orthotic brace device, comprising:
- a) a foot plate configured to be disposed under a user's foot and between the user's foot and a shoe worn on the user's foot;
- b) a rearward elongated spring having a proximal end attached to the foot plate and extending substantially vertically to an opposite end configured to be coupled to the user's leg;
- c) the rearward spring being flexible and deflectable during use through a deflection range and resilient or elastic to provide a resistance force to deflection and movement of the rearward spring with respect to the foot plate and between the user's foot and leg;
- d) a forward elongated spring having a proximal end attached to the foot plate and extending substantially vertically therefrom to a distal end configured to be engaged by the rearward spring;
- e) the forward spring being flexible to deflect and resilient or elastic to provide additional resistance force to deflection and movement when engaged by the rearward spring;
- f) the forward spring being spaced-apart forwardly with respect to the rearward spring from the proximal end at the foot plate to the distal end and positioned so that the rearward spring engages the forward spring during a distal portion of the deflection range; and
- g) the forward and rearward springs include a composite material with a fiber in a resin matrix.

* * * * *